United States Patent
Wider et al.

(10) Patent No.: US 8,781,546 B2
(45) Date of Patent: Jul. 15, 2014

(54) SYSTEM AND METHOD FOR DIFFERENTIATING BETWEEN TISSUE-SPECIFIC AND SYSTEMIC CAUSES OF CHANGES IN OXYGEN SATURATION IN TISSUE AND ORGANS

(75) Inventors: Michael D. Wider, Pleasant Ridge, MI (US); Ronald A. Widman, Macomb, MI (US); Oleg Gonopolskiy, West Bloomfield, MI (US)

(73) Assignee: Covidien LP, Mansfield, MA (US)

( * ) Notice: Subject to any disclaimer, the term of this patent is extended or adjusted under 35 U.S.C. 154(b) by 1219 days.

(21) Appl. No.: 12/421,990

(22) Filed: Apr. 10, 2009

(65) Prior Publication Data

US 2009/0259117 A1    Oct. 15, 2009

Related U.S. Application Data

(60) Provisional application No. 61/044,318, filed on Apr. 11, 2008.

(51) Int. Cl.
*A61B 5/1455* (2006.01)
*A61B 5/00* (2006.01)

(52) U.S. Cl.
CPC ........... *A61B 5/14551* (2013.01); *A61B 5/7264* (2013.01)
USPC ........................................................ 600/323

(58) Field of Classification Search
USPC ........................................................ 600/323
See application file for complete search history.

(56) References Cited

U.S. PATENT DOCUMENTS

| | | | |
|---|---|---|---|
| 6,353,226 B1 * | 3/2002 | Khalil et al. | 250/341.8 |
| 6,615,065 B1 * | 9/2003 | Barrett et al. | 600/340 |
| 7,043,287 B1 * | 5/2006 | Khalil et al. | 600/310 |
| 7,532,919 B2 * | 5/2009 | Soyemi et al. | 600/323 |
| 7,774,047 B2 * | 8/2010 | Yamashita et al. | 600/476 |
| 8,017,407 B2 * | 9/2011 | Navon | 436/164 |
| 8,396,526 B2 * | 3/2013 | Benni | 600/323 |
| RE44,735 E * | 1/2014 | Barrett et al. | 600/322 |
| 2003/0144584 A1 * | 7/2003 | Mendelson | 600/323 |
| 2004/0024297 A1 * | 2/2004 | Chen et al. | 600/323 |
| 2005/0083193 A1 * | 4/2005 | Al-Ali | 340/511 |
| 2006/0063995 A1 * | 3/2006 | Yodh et al. | 600/323 |
| 2007/0024946 A1 * | 2/2007 | Panasyuk et al. | 359/253 |
| 2007/0038042 A1 * | 2/2007 | Freeman et al. | 600/310 |
| 2008/0009689 A1 * | 1/2008 | Benaron et al. | 600/323 |
| 2008/0188727 A1 * | 8/2008 | Benaron et al. | 600/323 |
| 2008/0287758 A1 * | 11/2008 | Benaron et al. | 600/339 |
| 2008/0300474 A1 * | 12/2008 | Benni et al. | 600/331 |
| 2009/0048502 A1 * | 2/2009 | Benaron et al. | 600/328 |
| 2009/0187086 A1 * | 7/2009 | Benaron et al. | 600/323 |
| 2009/0253968 A1 * | 10/2009 | Cho et al. | 600/301 |
| 2010/0292549 A1 * | 11/2010 | Shuler | 600/324 |

OTHER PUBLICATIONS

International Search Report Dated Aug. 3, 2009.

* cited by examiner

*Primary Examiner* — Sean Dougherty
*Assistant Examiner* — Michael C Stout
(74) *Attorney, Agent, or Firm* — Harness, Dickey & Pierce, PLC

(57) ABSTRACT

A method for monitoring oxygen saturation that includes the following steps: (i) measuring an oxygen saturation of a target area of a person or animal over time; (ii) measuring an oxygen saturation of a reference area of the person or animal over time; and (iii) classifying the oxygen saturation status of the target area based upon a comparison of the oxygen saturation of the target area relative to the oxygen saturation of the reference area over time.

15 Claims, 4 Drawing Sheets

SYSTEM AND METHOD FOR DIFFERENTIATING BETWEEN TISSUE-SPECIFIC AND SYSTEMIC CAUSES OF CHANGES IN OXYGEN SATURATION IN TISSUE AND ORGANS

CROSS-REFERENCE TO RELATED APPLICATION

This Application claims the benefit of U.S. Provisional Application 61/044,318 filed on Apr. 11, 2008.

BACKGROUND OF THE INVENTION

The ability to determine oxygen saturation of hemoglobin in different parts of a person or animal's body is useful for a variety of known medical reasons. One method of determining oxygen saturation of hemoglobin is through transcutaneous near infrared spectroscopy (NIRS). Various types of equipment that use NIRS to measure oxygen saturation of hemoglobin in arteries and tissue are known to those of skill in the art and are commercially-available. For example, Somanetics Corporation of Troy, Mich. commercially offers for sale its INVOS System, which uses NIRS to estimate regional hemoglobin oxygen saturation in tissue, including in the brain, muscles and organs, such as the kidney or gut. U.S. Pat. Nos. 6,615,065 and 5,902,235 assigned to Somanetics Corporation, further illustrate devices for measuring oxygen saturation of hemoglobin in tissue. Devices that measure oxygen saturation of hemoglobin, such as Somanetics' INVOS system and the devices described in the above-referenced patents owned by Somanetics are generally referred to as oximeters.

Oximeters that measure oxygen saturation in the arteries are referred to as pulse oximeters while tissue oximeters such as the Somanetics INVOS System are useful for measuring venous weighted oxygen saturation of hemoglobin in regional tissue. It is widely accepted in the medical arts that the venous oxygen saturation reflects the balance between oxygen delivery to the tissue and tissue demand for oxygen. There is a long-standing medical need to be able to determine whether a change in the oxygen saturation of hemoglobin in various regional tissue areas is the result of systemic oxygen delivery conditions, including but not limited to hypoxemic hypoxia, hypovolemic hypoxia, anemia and the like or local site-specific oxygen delivery conditions, such as restricted blood flow to a particular organ. For example, differentiating between systemic oxygen delivery conditions and local site-specific oxygen delivery conditions may be important in the management of pediatric patients who have congenital heart disease; in identifying patients who are at risk for developing necrotizing enterocolitis (NEC); and in assisting surgeons to adjust procedures to prevent organ damage from ischemia.

Those skilled in the art will be aware that changes in the delivery of oxygen can be due to changes in the blood and hemoglobin oxygen transport function as well as to various changes in the physiologic systems that deliver blood to the tissue and hence changes in tissue oxygen saturation will reflect changes in those functions and systems and may be used to monitor functions and systems. Those persons skilled in the art will recognize many other benefits of being able to determine whether a change in oxygen delivery to the tissues is due to systemic or local causes The inventive methods and systems described hereinafter provide a method and system for differentiating between global or systemic hypoxia on the one hand and local or site-specific tissue ischemia on the other hand.

DETAILED DESCRIPTION OF THE INVENTION

An oximeter is used to measure oxygen saturation of hemoglobin over time in a target area and in a reference area of the body of a person or animal. The target area is the tissue or organ (including the brain) being evaluated. In one embodiment, the reference area can be a tissue area or organ (including the brain) remote from the target area. For example, the target area could be a person's kidney and the reference area could be the brain, gut or leg of the person. In another embodiment, the reference area could be the shallow tissue, such as skin, muscle or bone, between the target area and the oximeter sensor. For example, where the target area is a person's kidney, the reference area could be the shallow tissue, i.e., skin and muscle, between the person's kidney and the oximeter sensor. The change over time in oxygen saturation of hemoglobin in the target area is compared with that in the reference area. When the change in oxygen saturation in the target area and the reference area are approximately the same, it is determined that the change is due to global systemic causes. In contrast, when there is a change in the oxygen saturation in the target area but the oxygen saturation remains approximately constant in the reference area, it is determined that the change is due to local tissue-specific causes.

Figure 1:
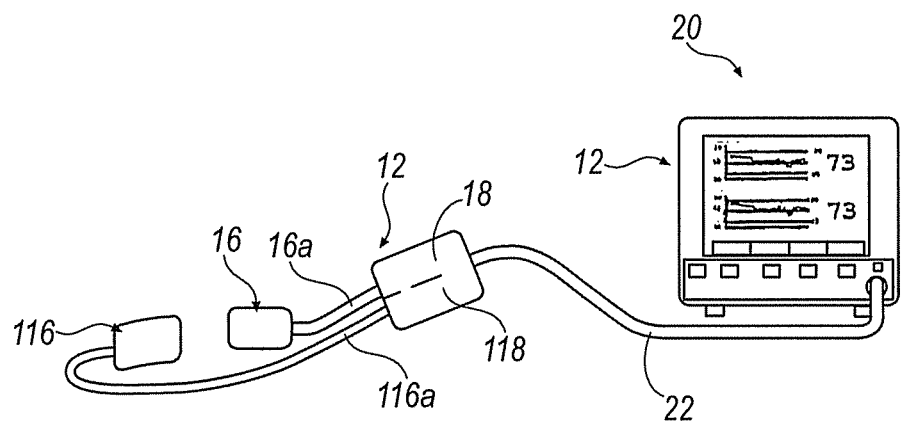
FIG. 1 is an illustration of an exemplary oximeter assembly.

An exemplary oximeter assembly useful to measure oxygen saturation levels for the purposes described in connection with this invention is set forth in U.S. Pat. No. 6,6115,065 (the '065 patent), which is incorporated herein by reference. Of course, other commercially-available oximeters (now or in the future) could be used and/or adapted to be used to measure oxygen saturation levels for the purposes of this invention. FIG. 1 herein generally depicts an oximeter assembly 12 having two NIRS sensors 16, 116, like that described in the '065 patent. The sensors 16, 116 are connected to a processor and display unit 20, which provides a central control and processing station (sometimes referred to as the "oximeter"), by a corresponding electrical cable 16A, 116A, which join one another at a dual-channel coupler/pre-amp 18, 118 and then (preferably) proceed to the control and processor 20 as an integrated, multiple-conductor cable 22. The sensors 6, 116 are intended to be positioned in contact with a person or animal's skin, near the target tissue (e.g., kidney, gut, brain, etc.) to be monitored. While FIG. 1 illustrates an oximeter assembly having two NIRS sensors, oximeter assemblies having more or less than two sensors are also contemplated.

Figure 2:
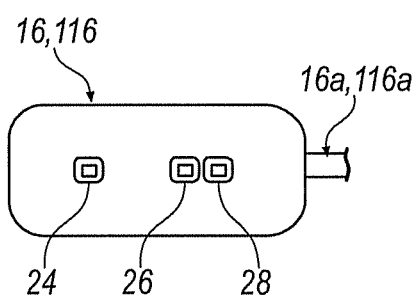
FIG. 2 is an illustration of an exemplary NIRS sensor used with an oximeter assembly.

FIG. 2 illustrates in more detail an exemplary NIRS sensor 16, 116. Each exemplary sensor 16, 116 includes an electrically actuated light source 24 for emitting the selected examination spectra (e.g., two or more narrow-bandwidth LEDs, whose center output wavelengths correspond to the selected examination spectra), together with a pair of light detectors 26, 28 (e.g., photodiodes) which are located at selected and mutually different distances from the source 24. Individual electrical conductors inside of cables 16A, 116A provide operating power to the sources 24, while others carry output signals from the detectors 26, 28, which are representative of detected light intensities received at the respective detector locations and must be conveyed to the processor unit 20, where processing takes place. The preferred configuration of sensors 16, 116 includes both a "near" detector 26 and a "far" detector 28. The "near" detector 26 principally receives light from source 24 whose mean path length is primarily confined to the shallow tissue layers, e.g., skin, tissue, bone, etc. above the target area, e.g., brain, kidney, gut. The "far" detector 28 receives light spectra that has followed a longer mean path length and traversed a substantial amount of the target tissue.

The oximeter 20 receives the signals indicative of the intensity of the light detected by the sensors 16, 116, which is indicative of the oxygen saturation of the hemoglobin in the area under the sensors. The oximeter includes an internal processor, which processes the signals to display a nominal measurement of the oxygen saturation levels (expressed as rSO2) detected by each sensor 6, 116 over time on a display screen. As a result, the oxygen saturation level detected by each sensor 6, 116, positioned at different places (e.g., a target area and a reference area) on the person or animal, can be displayed concurrently as a function of time. Alternatively, the oximeter 20 may process the signals so as to display the oxygen saturation detected by the "far" detector 28 (measuring the oxygen saturation in the target area) as a percentage or ratio of the oxygen saturation detected by the "near" detector (measuring the oxygen saturation in the shallow tissue above the target area) over time.

It has been recognized by the inventors that where a target area exhibits a change in oxygen saturation over time but a reference area remains stable or does not show an approximately equal change, the reason for the change in oxygen saturation in the target area is a local tissue-specific condition. It has also been recognized by the inventors that, in contrast, a target tissue that exhibits a change in oxygen saturation over time that parallels a change in oxygen saturation of a reference area over the same time period is caused by a global systemic condition. This relationship can be seen by the examples shown in FIGS. 3-6, discussed in detail hereinafter.

The oximeter 20 may further be equipped with software and/or hardware that identify the patterns in oxygen saturation over time (described above) that differentiate between global systemic causes and local tissue-specific causes, as well as other conditions. For example, the oximeter 20 may be programmed to identify and provide visual or audible indicators of states such as (a) stable and adequate global oxygen delivery; (b) compromised global systemic oxygen delivery; (c) compromised local tissue-specific oxygen delivery; and (d) impending shock states.

Figure 3:
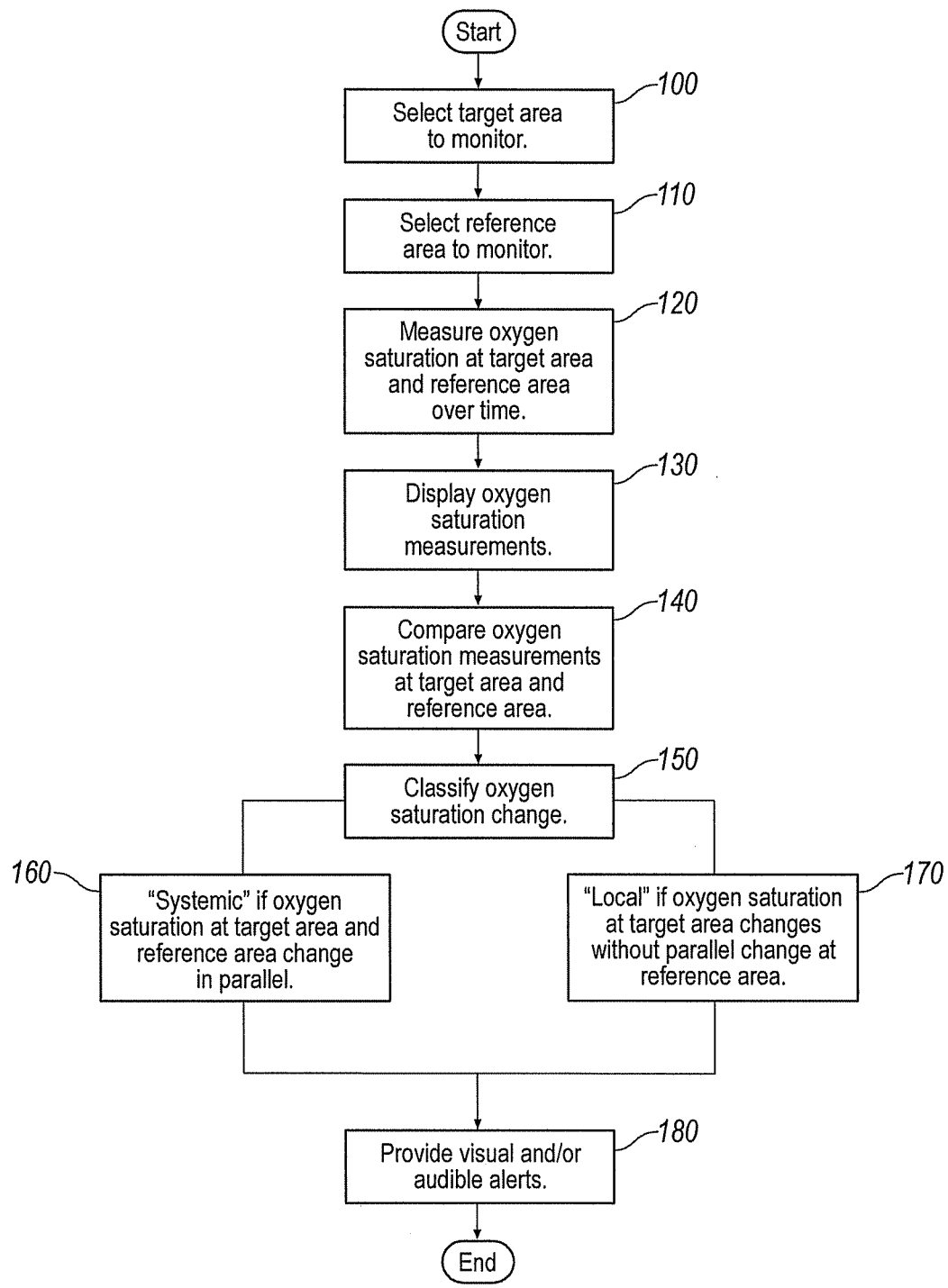
FIG. 3 is a flowchart that describes a method of classifying a change in oxygen saturation levels in tissue of a person or animal.

FIG. 3 is a flowchart that illustrates an exemplary method for differentiating between global systemic causes and local tissue-specific causes of changes in oxygen saturation of a target area. A target area of the person or animal is selected (step 100). The target area may be one of various organs or tissue areas of a person or animal's body, such as a kidney, gut, leg, etc. A reference area of the person or animal is selected (step 110). The reference area may be another organ or tissue area remote from the target area, or it may be the shallow tissue, such as skin, muscle or bone, located between the target area and the oximeter sensor. Oxygen saturation levels are measured at the target area and at the reference area over time (step 120). The oxygen saturation levels at the target area and/or the reference area may be displayed on a display screen (step 130). In some embodiments, the oxygen saturation levels at the target area are displayed in a different color from those illustrating the oxygen saturation level in the reference area. The oxygen saturation levels at the target area and the reference area are compared (step 140). If the oxygen saturation level at the target area changes over time, but the oxygen saturation level at the reference area does not change over time parallel to the change at the target area, it is determined that the cause of the oxygen saturation level at the target area is a local tissue-specific condition (step 150). If the oxygen saturation level at the target area changes over time, and the oxygen saturation level at the reference area changes over time in a parallel fashion to the change at the target area, it is determined that the cause of the oxygen saturation level at the target area is a global systemic condition (step 160). Differentiating visual and/or audible alerts may be provided to identify various states of the person or animal, such as (a) stable and adequate global oxygen delivery; (b) compromised global systemic oxygen delivery; (c) compromised local tissue-specific oxygen delivery; and (d) impending shock states (step 170).

Figure 4:
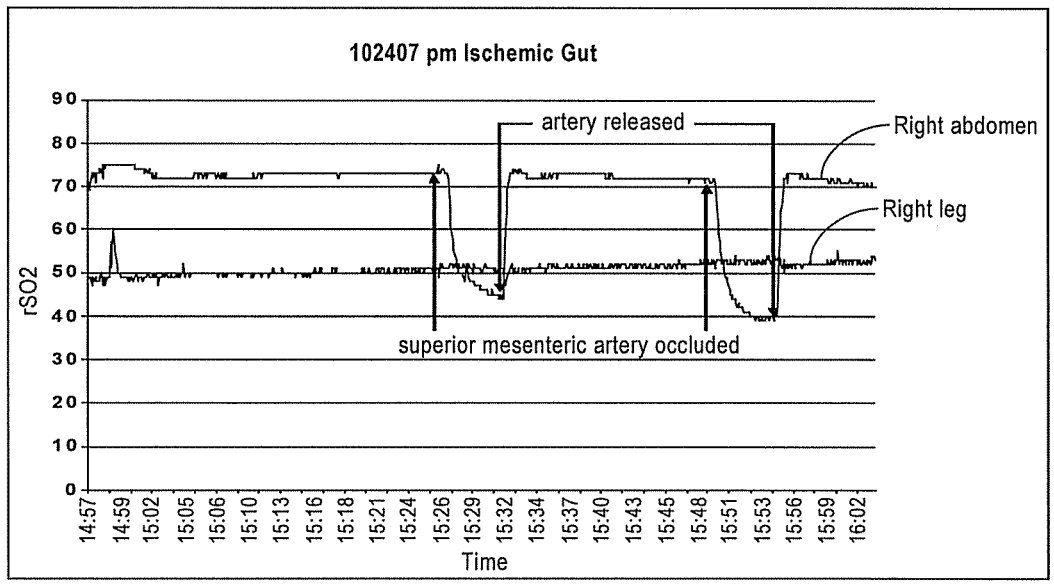
FIG. 4 is a first display of oxygen saturation measurements.

FIGS. 4-7 show exemplary displays from an oximeter 20 that were obtained by placing sensors 6, 116 over various sites on a piglet's body. FIG. 4 illustrates a test where sensors 6, 16 were placed over the gut (target area) and leg (reference area) of a piglet. Blood flow to the gut was interrupted, causing a drop in tissue hemoglobin oxygen saturation (expressed as rSO2) in the gut, but not in the leg. From the display shown in FIG. 4, it could be determined that the cause of the change in oxygen saturation in the gut was caused by a local tissue-specific condition.

Figure 5:
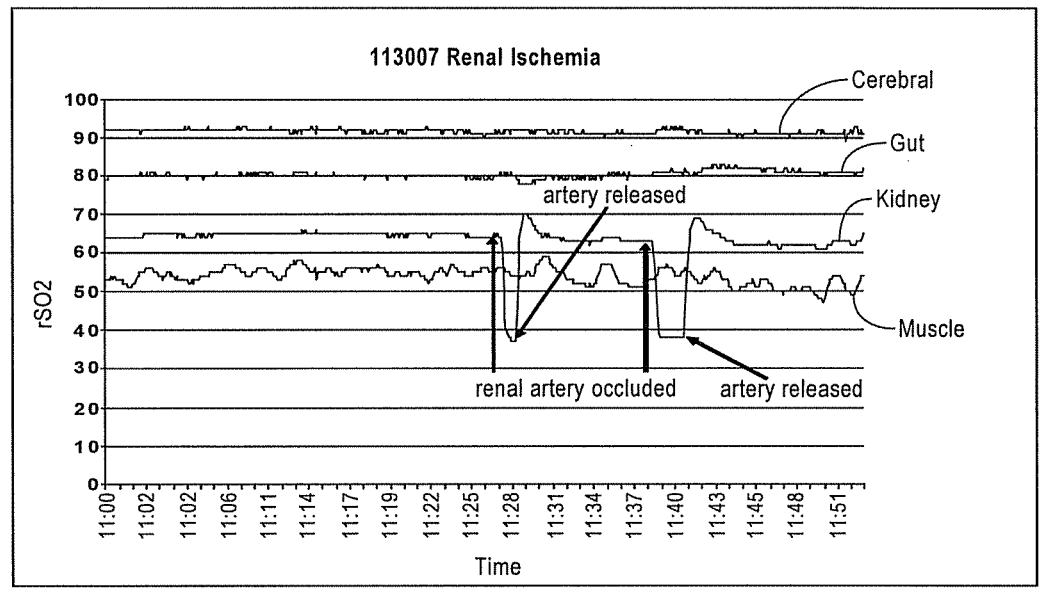
FIG. 5 is a second display of oxygen saturation measurements.

FIG. 5 illustrates a test where an oximeter having four sensors (such as sensors 6 and 16 in FIGS. 1, 2) was used, and the sensors were placed over the kidney (target area), head, gut and leg (reference areas) of a piglet. Blood flow to the kidney was interrupted, causing a drop in tissue hemoglobin oxygen saturation in the kidney (expressed as rSO2), but not in the leg, head or gut. From the display shown in FIG. 5, it could be determined that the cause of the change in oxygen saturation in the kidney was caused by a local tissue-specific condition.

Figure 6:
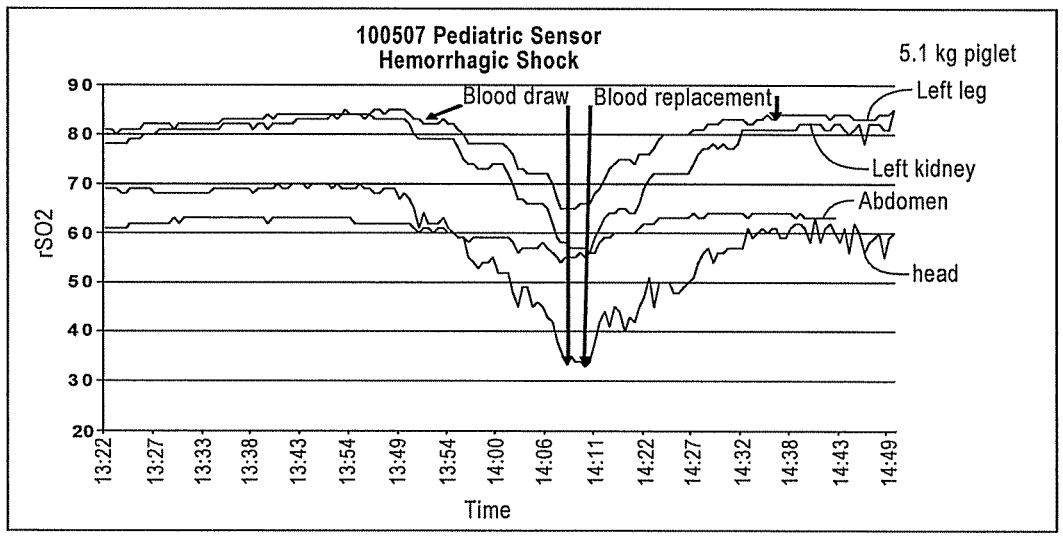
FIG. 6 is a third display of oxygen saturation measurements.

FIG. 6 illustrates a test where an oximeter having four sensors was used, and the sensors were placed over the right kidney (target area), left leg, right abdomen and the head (reference areas) of a piglet. Sequential blood draws of 20 cc were performed reducing the amount of blood available to perfuse the tissues and hence decreasing the amount of hemoglobin bound oxygen delivered to the tissues, which caused the tissue hemoglobin oxygen saturation in all four tissues to drop in parallel. The blood was sequentially reinfused into the femoral artery in 20 cc aliquots, causing the tissue hemoglobin oxygen saturation to increase back to original levels in parallel. From the display shown in FIG. 6, it could be determined that the cause of the change in oxygen saturation right kidney, left leg, right abdomen and head was caused by a global systemic condition.

Figure 7:
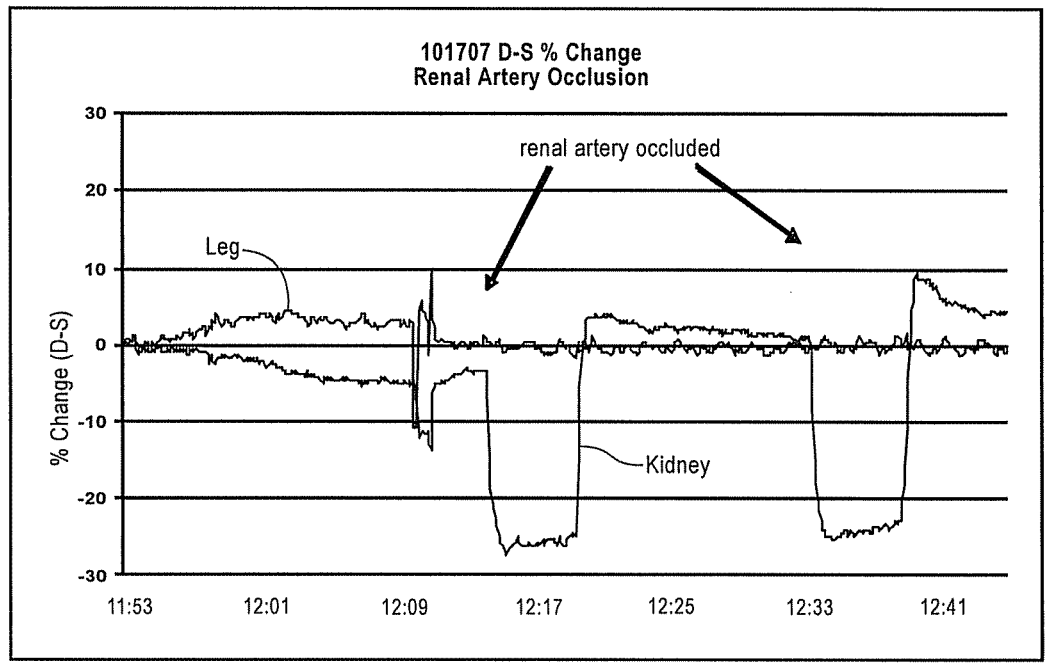
FIG. 7 is a fourth display of oxygen saturation measurements.

FIG. 7 illustrates a test where two sensors were placed over the right kidney and left leg, respectively, of a piglet. Each sensor was equipped, as described above, with a "near" detector and a "far" detector. Blood flow to the kidney was interrupted, causing a change in the "far" signal compared to the "near" signal received from the sensor placed over the kidney. This data is represented in FIG. 7 as a ratio or percentage change from baseline of the "far" signal minus the "near" signal over time. The negative change in the ratio of the difference between the "far" signal to the "near" signal indicates a local tissue specific decrease in blood flow to the kidney was the cause for the change in oxygen saturation. Also illustrated in FIG. 7 is the ratio of the change from baseline of the "far" signal minus the "near" signal received from the sensor placed over the leg. Notably, that ratio stayed fairly constant over time, confirming that the leg was not affected by the local tissue-specific cause of the oxygen saturation change in the kidney.

Reference in the specification to "one example," "an example," "one approach," or "an application" means that a particular feature, structure, or characteristic described in connection with the example is included in at least one example. The phrase "in one example" in various places in the specification does not necessarily refer to the same example each time it appears.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A method for classifying a condition causing a change in oxygen saturation of hemoglobin in a target area of a body of a person or animal as either a systemic condition or a local condition, comprising:
    identifying a target area and a reference area on the body of a human or animal, where said target area is chosen from the group consisting of tissue and organs and wherein said reference area includes shallow tissue located above the target area such that the tissue or organ chosen for said target area is different from the shallow tissue of said reference area;
    periodically measuring oxygen saturation in the target area and an oxygen saturation in the reference area;
    periodically comparing the oxygen saturation in the target area to the oxygen saturation in the reference area;
    classifying the condition causing the change in oxygen saturation of hemoglobin in the target area as systemic or local based upon said comparison; and
    identifying an impending shock state of the target area based at least in part on the oxygen saturation in the target area relative to the oxygen saturation in the reference area.

2. The method of claim 1, wherein the condition is classified as "systemic" if the oxygen saturation in the target area changes and the oxygen saturation in the reference area changes in a parallel fashion to the target area over time.

3. The method of claim 1, wherein the condition is classified as "local" if the oxygen saturation in the reference area does not change in a parallel fashion to the oxygen saturation in the target area over time.

4. The method of claim 1, wherein the measuring step comprises:
    receiving signals from a first near-infrared spectroscopy (NIRS) sensor located on the body of the person or animal near the target area;
    receiving signals from a second NIRS sensor on the body of the person or animal near the reference area;
    calculating an oxygen saturation of the target area from said signals received from said first NIRS sensor and calculating an oxygen saturation of the reference area from said signals received from said second NIRS sensor.

5. The method of claim 1, wherein the measuring step comprises:
    receiving signals from a first optical detector located on a sensor near the target area; and
    receiving signals from a second optical detector on said sensor.

6. The method of claim 5, wherein the comparing step comprises calculating a ratio between said signal received from said first optical detector and said signal received from said second optical detector at a given time.

7. The method of claim 1, further comprising selecting another reference area remote from the target area.

8. The method of claim 1, further comprising the step of visually displaying the periodic oxygen saturations of the target area and the reference area concurrently.

9. The method of claim 8, further comprising the step of visually displaying the periodic oxygen saturations of the target area and the reference area in a manner that are visually distinctive from each other.

10. A method for monitoring oxygen saturation, comprising:
    measuring an oxygen saturation of a target area of a person or animal over time, where said target area is chosen from the group consisting of tissue and organs;
    measuring an oxygen saturation of a reference area of the person or animal over time, where said reference area includes shallow tissue located above said target area, wherein the shallow tissue of said reference area is different from the tissue or organs chosen for said target area;
    classifying the oxygen saturation status of the target area based upon a comparison of the oxygen saturation of the target area relative to the oxygen saturation of the reference area over time, wherein the oxygen saturation status indicates an impending shock state of the target area.

11. The method of claim 10, wherein the classifying step comprises classifying the oxygen saturation status of the target area to be compromised if the oxygen saturation of the target area decreases substantially over time.

12. The method of claim 11, wherein the classifying step comprises:
- classifying the compromised status as being a result of a systemic condition if said oxygen saturation of said reference area decreases in parallel to the oxygen saturation of said target area over time;
- classifying the compromised status as being a result of a local condition if said oxygen saturation of said reference area does not decrease in parallel to the oxygen saturation of said target area over time; and
- classifying the oxygen saturation status to be stable and adequate if the oxygen saturation of the target area and the oxygen saturation of the reference area are above a pre-determined threshold over time.

13. The method of claim 12, wherein said target area is the brain of the person or animal, and wherein the classifying step comprises classifying the oxygen saturation status to be indicative of the impending shock if the oxygen saturation level of the brain is decreasing over time and the oxygen saturation of the reference area is stable.

14. The method of claim 13, further comprising the step of providing a visual or audible indicator of the classified oxygen saturation status.

15. A method for classifying a condition causing a change in blood flow determined by oxygen saturation of hemoglobin in a target area of a body of a person or animal as either a systemic condition or a local condition, comprising:
- identifying a target area and a reference area on the body of a human or animal, wherein the target area includes an organ or tissue and wherein the reference area includes shallow tissue different from the organ or tissue of said target area and located near said target area;
- periodically measuring oxygen saturation in the target area and an oxygen saturation in the reference area;
- periodically comparing the oxygen saturation in the target area to the oxygen saturation in the reference area; and
- classifying the condition causing the change in blood flow in the target area as systemic or local based upon said comparison; and
- identifying an impending shock state of the target area based at least in part on the oxygen saturation in the target area relative to the oxygen saturation in the reference area.

* * * * *